(12) United States Patent
Higuchi et al.

(10) Patent No.: US 7,833,485 B2
(45) Date of Patent: Nov. 16, 2010

(54) SAMPLE PREPARING APPARATUS

(75) Inventors: Hideyuki Higuchi, Kobe (JP); Hiroshi Kuroda, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 1001 days.

(21) Appl. No.: 11/223,495

(22) Filed: Sep. 8, 2005

(65) Prior Publication Data

US 2006/0051241 A1    Mar. 9, 2006

(30) Foreign Application Priority Data

Sep. 8, 2004    (JP) .............................. 2004-261707

(51) Int. Cl.
*B01L 3/02*    (2006.01)
(52) U.S. Cl. ..................... 422/100; 422/65; 422/67; 422/102; 422/104; 700/40; 700/90
(58) Field of Classification Search ................. 422/100, 422/63, 65, 67, 102, 104; 700/40, 90
See application file for complete search history.

(56) References Cited

U.S. PATENT DOCUMENTS

| 5,209,903 A | 5/1993 | Kanamori et al. |
| 5,779,982 A * | 7/1998 | Aota et al. ................. 422/100 |
| 7,297,311 B2 * | 11/2007 | Tamura et al. ................ 422/63 |
| 2006/0063265 A1 * | 3/2006 | Welcher et al. ............... 436/43 |

* cited by examiner

*Primary Examiner*—Jyoti Nagpaul
(74) *Attorney, Agent, or Firm*—Brinks Hofer Gilson & Lione

(57) ABSTRACT

The sample preparing apparatus comprises a smear forming means for forming a sample smear on a slide glass, a print means for printing sample identification information on a slide glass, a mode selecting means for selecting one operating mode from among a plurality of operating modes including a print mode, and a control means for selectively controlling the print means and the smear forming means. The control means operates the print means without operating the smear forming means when the print mode is selected.

12 Claims, 8 Drawing Sheets

SAMPLE PREPARING APPARATUS

This application claims priority under 35 U.S.C. §119 to Japanese Patent Application No. 2004-261707 filed Sep. 8, 2004, the entire content of which is hereby incorporated by reference.

FIELD OF THE INVENTION

The present invention relates to a sample preparing apparatus, and specifically relates to a sample preparing apparatus capable of printing specimen identification information on a slide glass.

BACKGROUND

Conventional smear sample preparation devices are used to prepare smear samples of blood specimen by dropping blood or the like onto a slide glass and drawing the glass to smear the specimen for observation of the blood using a microscope or the like.

Synthetic blood examination devices are known which allow setting the smear condition for each sample based on measurement results from a blood analyzer that analyzes the blood sample in order to efficiently perform the examination work (for example, refer to U.S. Pat. No. 5,209,903).

Identification information, such as the specimen number, date, reception number, patient name and the like, is written on the slide glass with the blood smear in order to identify the blood. For example, an ID number representing the identification information is automatically printed on the slide glass in the apparatus cited in the above patent publication. Blood, however, has diverse characteristics, such as particle density, viscosity and the like, and at times, depending on the specimen, when it is difficult to prepare a smear sample suitable for observation using a conventional smear sample preparing apparatus.

In the case of such blood samples, since a clinical technician must manually prepare the smear sample, and a clinical technician must write the identification information to identify the blood, the examination operation is not sufficiently efficient.

BRIEF SUMMARY

The scope of the present invention is defined solely by the appended claims, and is not affected to any degree by the statements within this summary.

An object of the present invention is to provide a sample preparing apparatus capable of efficiently performing examination work.

DETAILED DESCRIPTION OF THE PREFERRED EMBODIMENTS

The preferred embodiments of the present invention are described hereinafter with reference to the drawings.

Figure 5:
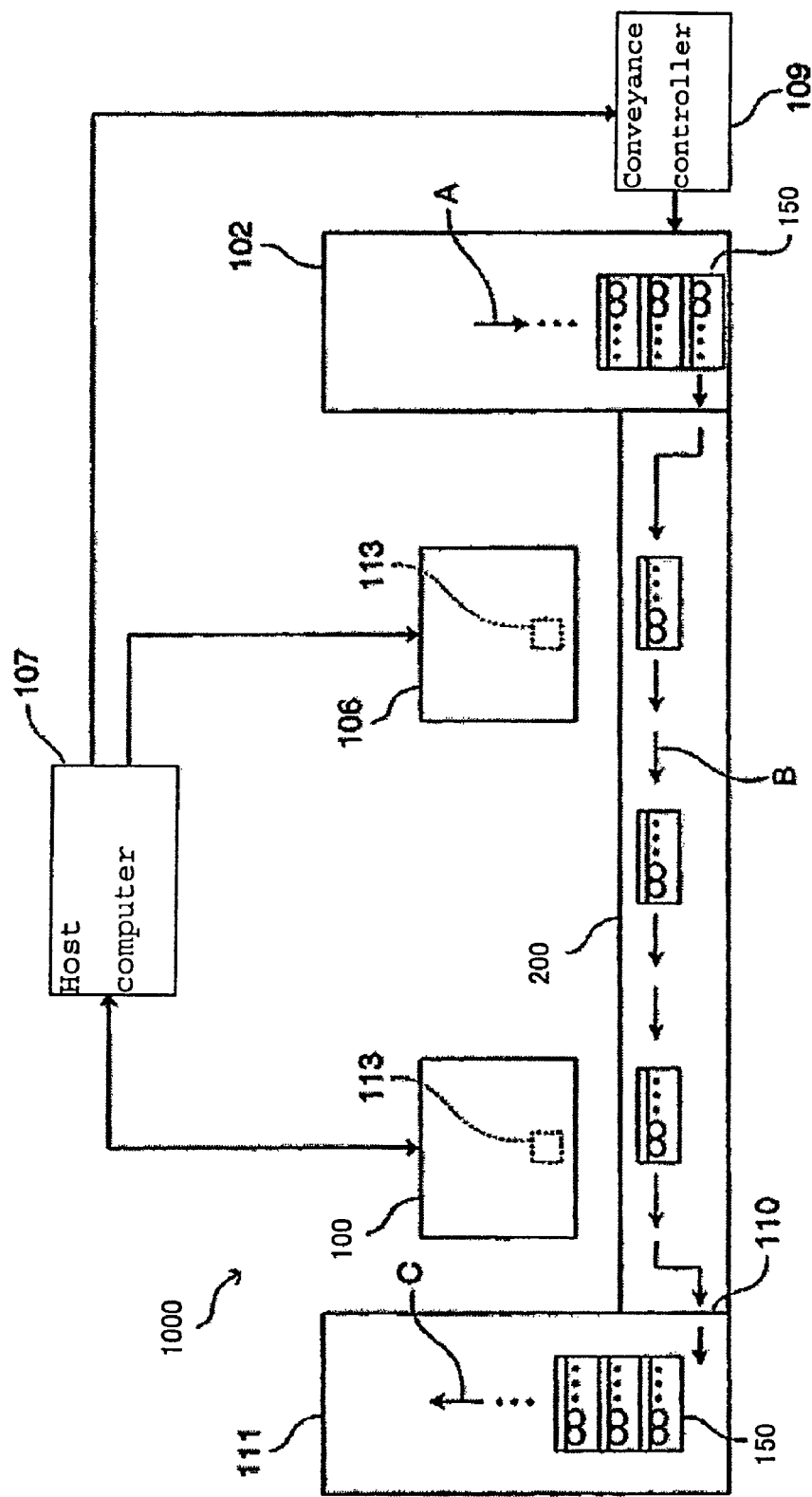
FIG. 5 shows the structure of the system including the conveyance device and sample preparing apparatus of the embodiment of the present invention.

FIG. 5 shows the structure of the system including the conveyance device and sample preparing apparatus of the embodiment of the present invention. The system 1000 shown in FIG. 5 is provided with a loader 102, conveyance device 200, and unloader 111, and a blood analyzer 106 and sample preparing apparatus 100 are arranged along the conveyance device 200.

The system 1000 includes a transport controller 109 for controlling the drive of the loader 102, conveyance device 200, and unloader 111, and a host computer 107 for issuing commands and information exchange with the blood analyzer 106, smear preparation apparatus 100, and conveyance controller 109. The host computer 107 collectivizes the sample preparing apparatus and blood analyzer related to blood examination. The specimen number, and identification information (date of specimen collection, reception number, name of person who provided the specimen and the like) corresponding to this specimen number are associated and stored in memory in the host computer 107.

Figure 1:
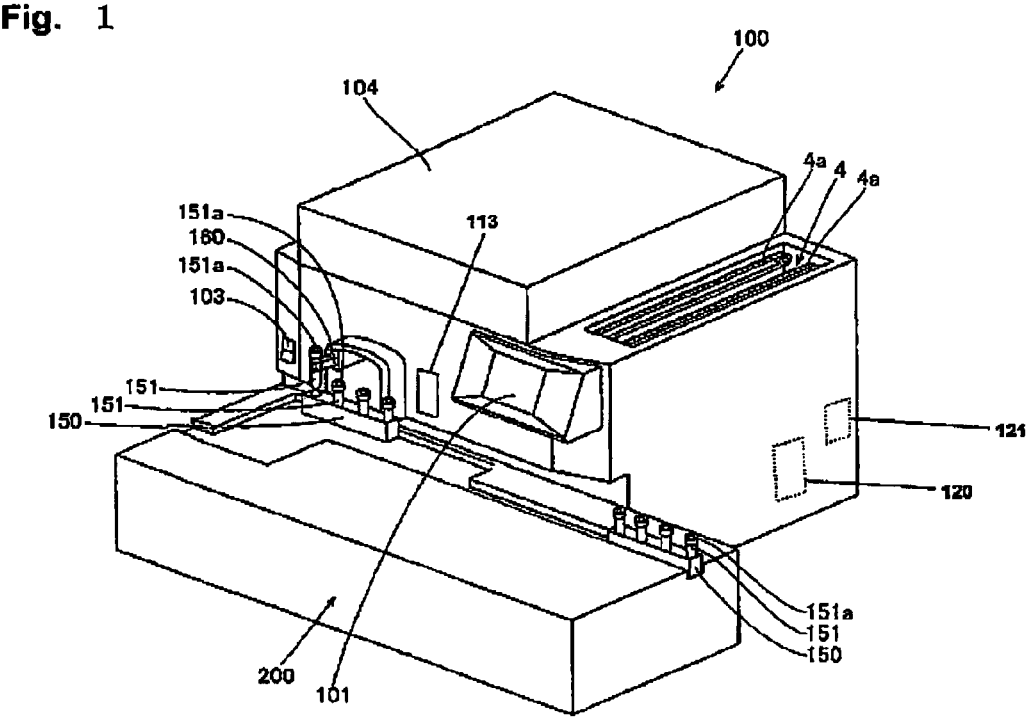
FIG. 1 is a perspective view showing the structure of the conveyance device and sample preparing apparatus of an embodiment of the present invention.

A plurality of sample racks 150 are provided in the loader 102. The sample rack 150 is transported in the arrow A direction and output from the loader 102 to the input end of the conveyance device 200 adjacent to the loader 102. FIG. 1 is a perspective view showing the structure of the conveyance device and sample preparing apparatus of an embodiment of the present invention. As shown in FIG. 1, each sample rack 150 holds a plurality of sample containers 151 that respectively contain blood samples. A barcode label (not shown in the drawing) representing the specimen identification information (ID) is adhered to each sample container 151.

As shown in FIG. 5, the sample rack 150 is transported in the Arrow B direction by the conveyance device 200, so as to pass in front of the blood analyzer 106 and sample preparing apparatus 100, and arrive at the output end of the conveyance device 200. The unloader 111 disposed adjacent to the output end 110 of the conveyance device 200 transports the sample rack 150 in the arrow C direction and accommodates the rack.

The operation of the system 1000 starts when sample racks 150 holding sample containers 151 are placed in the loader 102. The first sample rack 150 is moved in the arrow B direction by the conveyance device 200, and stops in front of the blood analyzer 106.

Then, the barcode of the first sample container 151 is read by a barcode reader 113. The blood analyzer 106 collects and analyzes the sample within the sample container 151, and reports (transmits) the analysis result together with the barcode to the host computer 107. The blood analyzer 106 repeats this process until the samples of all sample containers 151 of all sample racks 150 have been analyzed. The host computer 107 determines whether or not a sample requires blood smear preparation based on the analysis result.

Next, a sample rack 150 loaded only with samples that do not require smear preparation is moved past the front of the sample preparing apparatus 100 to the unloader 111 by the conveyance controller 109 that controls the conveyance device 200 based on commands from the host computer 107. A sample rack 150 loaded with samples that require smear preparation is stopped in front of the sample preparing apparatus 100 by the conveyance controller 109 that controls the conveyance device 200 based on commands from the host computer 107. The barcode of each sample container 151 is read by the barcode reader 113 of the sample preparing apparatus 100 and reported (transmitted) to the host computer 107. When the host computer 107 has determined that smear preparation is required, the sample preparing apparatus 100 collects a sample from the sample container 151 that requires sample preparation, and prepares a blood smear. Sample containers 151 that do not require smear preparation advance in the arrow B direction, and the next sample container 151 is stopped in front of the smear preparation apparatus 100.

Then, a sample rack 150, which has passed in front of the sample preparing apparatus 100, is moved to the unloader 111 by the conveyance device 200.

FIG. 1 is a perspective view showing the structure of the conveyance device and sample preparing apparatus of an embodiment of the present invention. As shown in FIG. 1, the conveyance device 200 is disposed on the front of the sample preparing apparatus 100. The sample preparing apparatus 100 includes a touch panel display and operation unit 101, power switch 103, cover 104, barcode reader 113, controller 120, and input/output (I/O) interface 121. The sample preparing apparatus 100 is provided with a hand 160 for transporting a blood-containing sample container 151 from the conveyance device 200 side to the sample preparing apparatus 100 side. A rubber stopper 151a seals the blood containing sample container 151. The I/O interface 121 has the function of receiving and transmitting information to the host computer 107.

Figure 2:
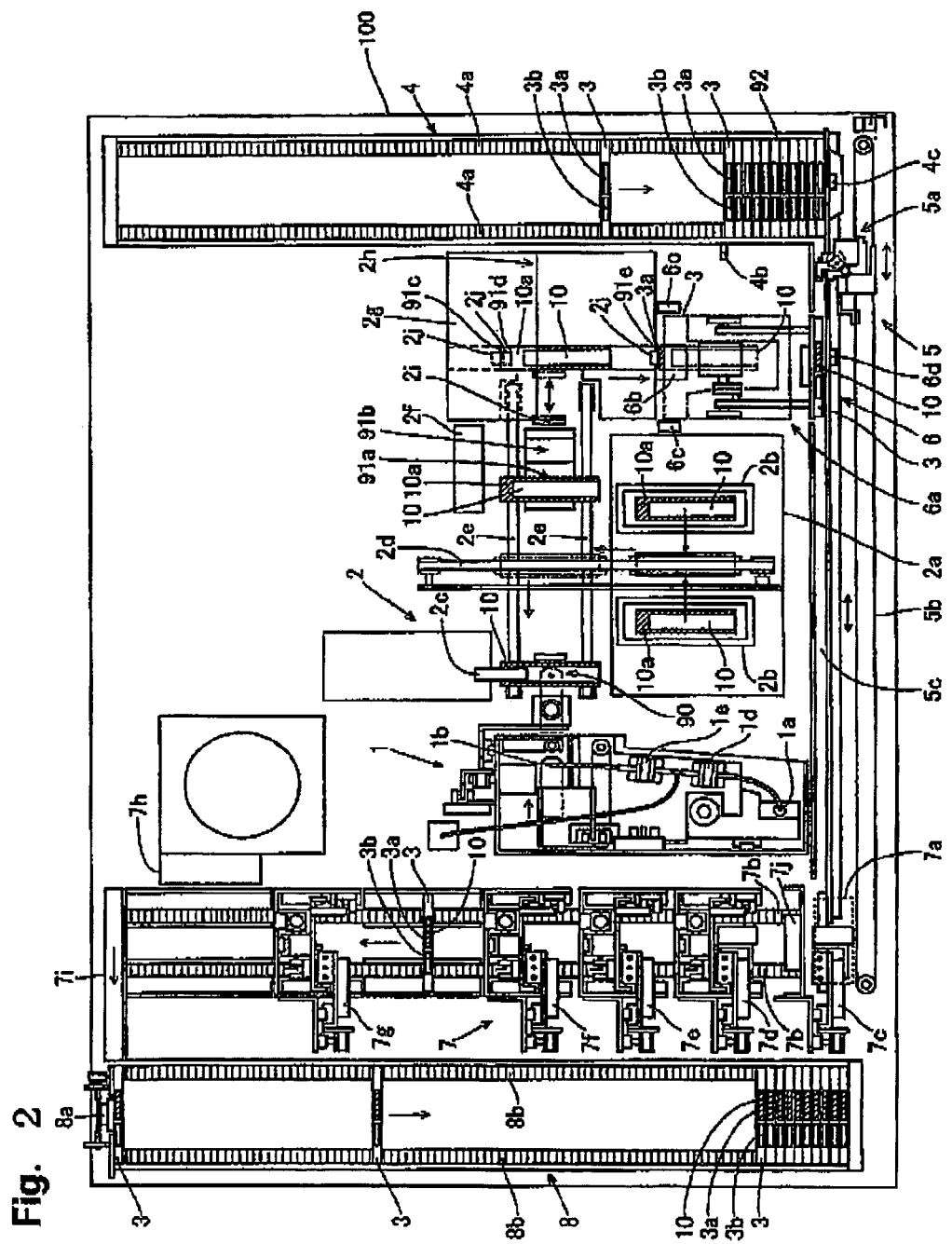
FIG. 2 is a top view showing the internal structure of the sample preparing apparatus of the embodiment of the present invention.

FIG. 2 is a top view showing the internal structure of the sample preparing apparatus of the embodiment of the present invention. As shown in FIG. 2, the sample preparing apparatus 100 is provided with a suction-dispensing mechanism 1, smear unit 2, print unit 2g, slide glass conveyor 2h, cassette holder 4, cassette conveyor 5, slide glass insert unit 6, stain unit 7, and storage unit 8. The suction-dispensing mechanism 1 has the functions of suctioning blood from a sample container 151 transported to the sample preparing apparatus 100 side by the hand 160, and dispensing the suctioned blood to a slide glass 10. The suction-dispensing mechanism 1, smear unit 2, print unit 2g, slide glass conveyor 2h, cassette holder 4, cassette conveyor 5, slide glass insert unit 6, stain unit 7, and storage unit 8 are controlled by the controller 120 (refer to FIG. 1).

The smear unit 2 is provided to supply a slide glass 10 to the dispensing-smear position 90, and smear and dry the blood dispensed to the slide glass 10. The smear unit 2 is provided with a slide glass supply unit 2a, slide glass holder 2b, drawing glass 2c, conveyor belts 2d and 2e, and fan 2f.

The print unit 2g is provided with a thermal transfer printer to print specimen information including sample identification information such as sample number, date, reception number, name and the like on the sample information print area 10a of the slide glass 10. The print unit 2g has the function of preparing a two-dimensional barcode based on specimen identification information such as sample number, date, reception number, name and the like.

Figure 6:
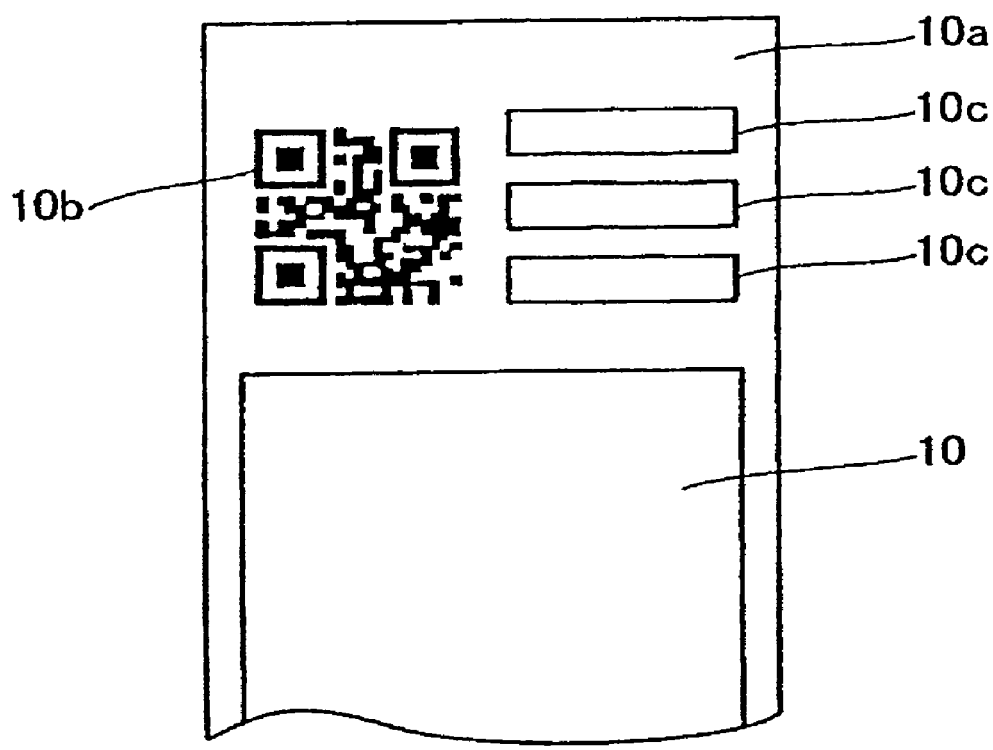
FIG. 6 is an enlargement of the specimen information printed area of the slide glass used in the sample preparing apparatus of the embodiment of the present invention.

FIG. 6 is an enlargement of the specimen information print area of a slide glass with sample information printed by the print unit 2g. As shown in FIG. 6, printed in the sample information print area 10a of the slide glass 10 are a two-dimensional barcode 10b that includes a specimen identification information such as sample number specifying the specimen, date the sample was collected, reception number to specify the reception of the sample, name of the person (patient) providing the sample and the like, and 3-lines of text 10c that includes the date and name in Chinese characters and the like.

The slide glass supply unit 2a has the function of supplying a slide glass 10 housed in the two slide glass holders 2b to the conveyor belt 2e using the conveyor belt 2d and a handling mechanism not shown in the drawing. The conveyor belt 2e is configured so as to transport a slide glass 10 to the dispensing-smearing position 90 and the drying positions 91a and 91b. The drawing glass 2c is configured so as to be movable to a position to contact with the slide glass 10, that is, movable in the length direction of the slide glass 10 so as to be capable of smearing blood dispensed onto the slide glass 10 at the dispensing-smearing position 90. The fan 2f is provided to dry the blood smear on the slide glass 10 transported to the drying positions 91a and 91b.

The slide glass conveyor 2h is provided to move the slide glass 10 from the end of the conveyor belt 2e to the print unit 2g, and move the printed slide glass 10 to the cassette 3 holding position. The slide glass conveyor 2h includes a horizontal moving piece 2i to move the slide glass 10 in a horizontal direction from the end of the conveyor belt 2e to the horizontal direction position 91c for printing, and a vertical moving piece 2j for moving the slide glass 10 in a vertical direction to a vertical direction position 91d for printing and the cassette 3 holding position 91e.

Figure 3:
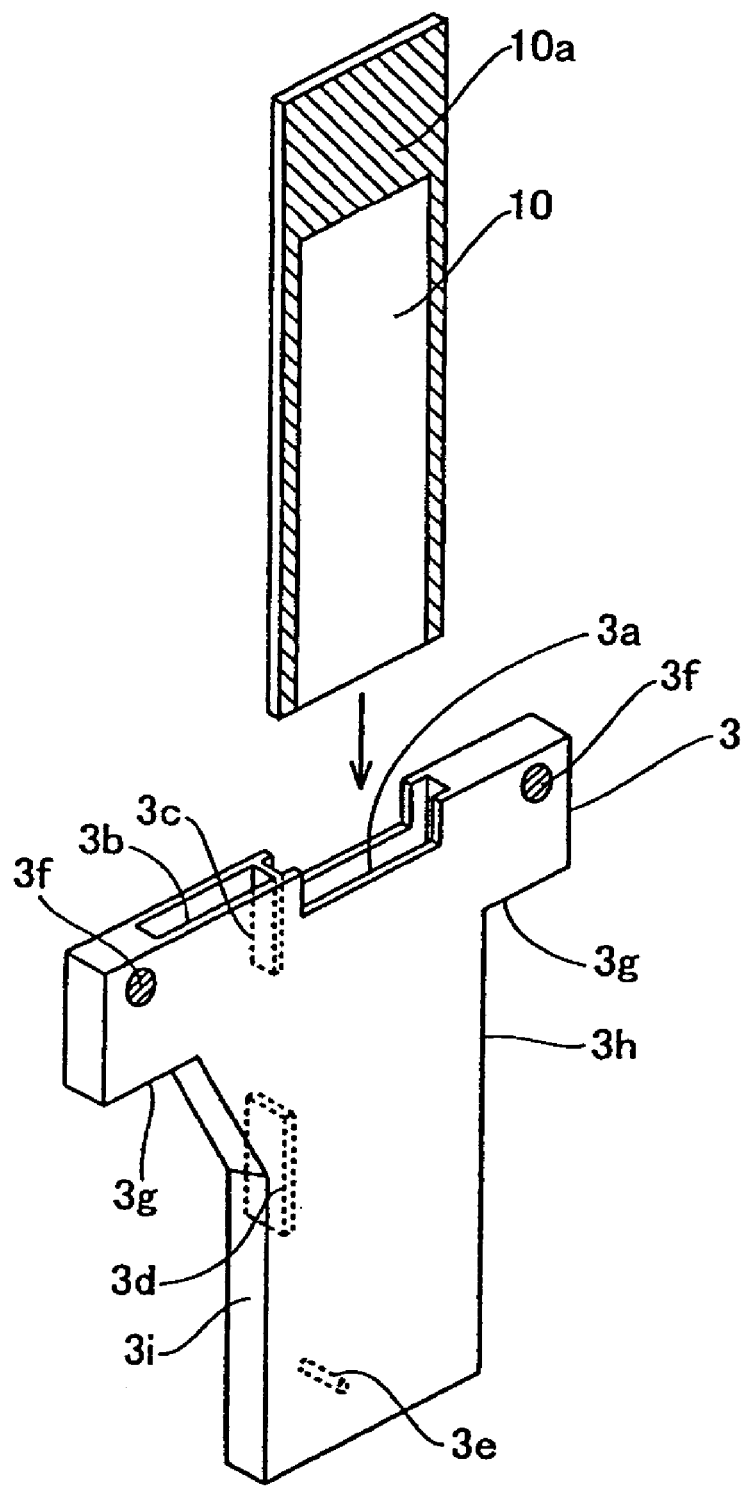
FIG. 3 is a perspective view showing the slide glass and cassette used in the sample preparing apparatus of the embodiment of the present invention.
Figure 4:
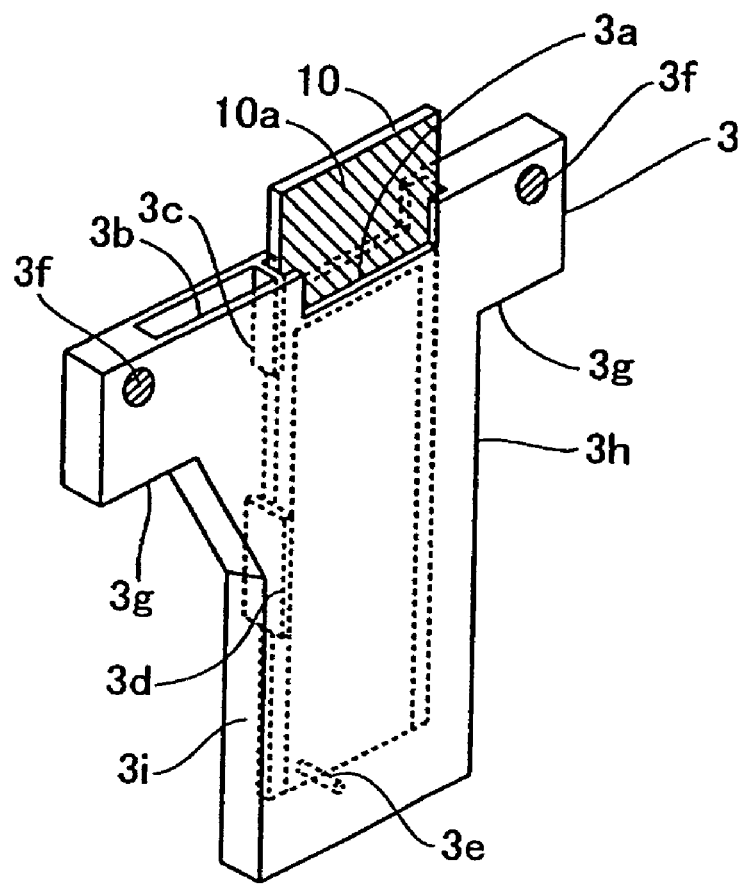
FIG. 4 is a perspective view showing the slide glass and cassette used in the sample preparing apparatus of the embodiment of the present invention.

FIGS. 3 and 4 are perspective views showing the glass slide and cassette used in the sample preparing apparatus of the embodiment of the present invention. As shown in FIGS. 3 and 4, the cassette 3 includes slide glass slot 3a, stain suction-dispensing hole 3b, partitions 3c and 3d, slide glass support 3e, two magnetically attractive members 3f configured by magnetically attractable metal, conveyor belt connector 3g, and side surfaces 3h and 3i. The slide glass slot 3a and the stain suction-dispensing hole 3b are internally connected. The cassette 3 is configured of resin so as to be capable of accommodating a smeared slide glass 10 and fluid (stain) used in the staining process, as shown in FIG. 3.

As shown in FIG. 2, the cassette holder 4 is provided to carry the cassette 3, and includes a feed belt 4a. Furthermore, the cassette holder 4 is provided with a remaining cassette sensor 4b for detecting when the number of remaining cassettes 3 at the standby position 92 of the cassette holder 4 are fewer than a predetermined number (for example, ten cassettes), and a loaded cassette sensor 4c for detecting whether or not a cassette 3 is loaded in the transport path 5c of the standby position 92 of the cassette holder 4.

The cassette conveyor 5 is provided to transport a cassette 3 that has been delivered from the cassette holder 4 to the slide glass insert unit 6 and stain unit 7. The cassette conveyor 5 includes a cassette transport member 5a movable in a horizontal direction, drive belt 5b for moving the cassette transport member 5a in a horizontal direction, and a transport path 5c for transporting a cassette 3 supplied from the cassette holder 4.

The slide glass insert unit 6 is provided to house the slide glass 10 in the slide glass slot 3a of the cassette 3. The slide glass insert unit 6 includes a cassette rotation mechanism 6a for positioning the cassette 3 in a horizontal direction such that a slide glass 10 is insertable, positioner 6b for positioning the height direction of the cassette 3 that has been positioned horizontally by the cassette rotation mechanism 6a, two positioners 6c for positioning the horizontally disposed cassette 3 in a vertical direction, and sensor 6d for detecting whether or not a slide glass 10 is housed in the cassette 3 positioned in the slide glass insert unit 6. Furthermore, the positioner 6b is also provided for positioning the cassette 3 in the height direction by abutting the back surface of a cassette 3 that has been horizontally rotated by the cassette rotation mechanism 6a. The two positioners 6c are also provided for positioning the cassette 3 in the vertical direction by correcting positional shifting of a cassette 3 in the vertical direction when a cassette 3 that has been horizontally rotated by the cassette rotation mechanism 6a has shifted vertically.

The stain unit 7 is provided to stain the blood smeared on a slide glass 10 by supplying a stain solution to the stain suction-dispensing hole 3b of a cassette 3 that has been transported by the cassette transport member 5a. The stain unit 7 includes feed member 7a for feeding a cassette 3 that has been transported by the cassette transport member 5a to a second suction-discharge unit 7d of the stain unit 7, conveyor belt 7b for transporting a cassette 3 that has been delivered from the feed member 7a, first through fifth suction-discharge units 7c~7g for supplying and discharging stain solution to the cassette 3, fan 7h for drying a stained slid glass 10, delivery mechanism 7i for delivering a cassette 3 from the conveyor belt 7b to the conveyor belt 8b side of the storage unit 8, and fan 7j for drying a slide glass 10 in the second suction-discharge unit 7d.

The storage unit 8 is provided for storing cassettes 3 that house slide glasses 10 stained by the stain unit 7. The storage unit 8 is provided with a feed member 8a for feeding a cassette 3 that has been brought from the conveyor belt 7b by the delivery mechanism 7i to the conveyor belt 8a of the storage unit 8, and a conveyor belt 8b for transporting a cassette 3 that has been brought from the feed member 8a. The feed member 8a of the storage unit 8 has a structure identical to that of the feed member 7a of the stain unit 7.

The operation of the sample preparing apparatus 100 of the present embodiment is described below. The sample preparing apparatus 100 operates in a sampler mode in which the apparatus 100 inquires of the host computer 107 whether or not sample smear preparation is required and suctions a sample if required from within a sample container 151 transported from the loader 102, and a manual mode in which a predetermined operating mode can be selected from among a plurality of operating modes and the apparatus 100 can be operated in the selected mode. The operating modes selectable in the manual mode include a smear-stain mode wherein a smear of a sample is formed on a slide glass and after sample identification information is printed, the prepared smear is stained; a smear mode wherein a smear of a sample is formed on a slide glass and sample identification information is printed, but the smear is not stained; a stain mode wherein a smear of a sample is formed and sample identification information is printed, then the sample is stained; and a print mode wherein sample identification information is printed on a slide glass, but the sample is not smeared nor is the smear stained.

The operation of the sample preparing apparatus in the sampler mode is described below.

When a sample rack 150 is placed in the loader 102 shown in FIG. 5 and the system 1000 is started, an operation is performed to convey the cassette 3 to the cassette holder 4 shown in FIG. 2. Specifically, the cassette 3 is first placed in the cassette holder 4. In this way the cassette 3 is transported to the cassette standby position 92 with the conveyer belt connector 3g (refer to FIG. 3) of the cassette 3 engaged with the feed belt 4a of the cassette holder 4. Furthermore, when there are fewer than a predetermined number (for example, ten) of cassettes 3 disposed at the cassette standby position 92 of the cassette holder 4, the remaining cassette sensor 4b detects the number of remaining cassettes 3 and a message such as [Please replace cassettes] or the like is displayed on the display operation unit 101 (refer to FIG. 1). The top cassette 3 among the cassettes 3 at the cassette standby position 92 is positioned in the transport path 5c. The cassette 3 disposed in the transport path 5c is detected by the cassette sensor 4c, and transported one by one to the slide glass insert unit 6 by the cassette conveyor 5. That is, the cassette 3 is transported to the slide glass insert unit 6 when the cassette transport member 5a forming the cassette transport path 5 pushes the side surface 3h (refer to FIG. 3) of the cassette 3 from the transport start position 93.

When the sample container 151 arrives in front of the barcode reader 113 of the sample preparing apparatus 100, the barcode of the sample container 151 is read, and the controller inquires to the host computer 107 whether or not a smear preparation is required for this sample container 151. When the reply from the host computer 107 specifies that smear preparation is required, suction and dispensing operations are performed.

In the suction and dispensing operation, first the hand 160 of the sample preparing apparatus 100 grasps the blood-containing sample container 151 from the sample rack 150. Then, the sample container 151 is lifted when the hand 160 is raised, and after the sample container 151 is agitated by rotating the hand 160, the sample container 151 is placed in the suction-dispensing mechanism 1 shown in FIG. 2. Next, a piercer 1a is inserted through the rubber stopper 151a of the sample container 151 and the blood is suctioned. During the suction operation, a valve 1d is opened (ON condition), and valve 1e is blocked (OFF condition). After the blood suctioning operation ends, the valve 1d is blocked (OFF condition), and the valve 1e is opened (ON condition). Thereafter, a pipette 1b is moved to the dispensing-smearing position 90 shown in FIG. 2, and subsequently the blood is dripped (dispensed) onto the slide glass 10 from the pipette 1b.

A smear operation is performed by the smear unit 2 in parallel with the suction-dispensing operation by the suction-dispensing mechanism 1. In the smear unit 2, the slide glass 10 is supplied to the dispensing-smear position 90 (refer to FIG. 2), and the blood dispensed to the slide glass 10 is smeared and dried. Specifically, a slide glass 10 housed in the two slide glass holders 2b of the slide glass supply unit 2a is supplied to the conveyor belt 2e using the conveyor belt 2d and a handling mechanism not shown in the drawing. Then, the slide glass 10 is transported to the dispensing-smear position 90 by the conveyor belt 2e. In this condition, the blood is dripped (dispensed) onto the slide glass 10 using the pipette 1b.

Thereafter, a drawing glass 2c is moved so as to abut the slide glass 10, and the blood dripped on the slide glass 10 at the dispensing-smear position 90 is smeared by a reciprocating movement of the slide glass 10 in the length direction. Thereafter, the smeared slide glass 10 is transported to the drying position 91a by the conveyor belt 2e. At the drying position 91a, the blood smeared on the slide glass 10 is dried with cool air by the fan 2f. The air drying of the slide glass 10 is performed twice at two adjacent drying positions 91a and 91b.

Thereafter, the smeared slide glass 10 is moved below the print unit 2g by the slide glass conveyor 2h. In parallel with the aforesaid operation, the print unit 2g receives sample information, which includes sample identification information from the host computer 107 through the controller 120, and creates a two-dimensional barcode from the sample information. Then, the print unit 2g prints the two-dimensional barcode and text on the sample information print area on the slide glass 10. Thereafter, the slide glass conveyor 2h moves the printed slide glass 10 to the slide glass insert unit 6.

Since the sample preparing apparatus 100 of the present embodiment is capable of printing two-dimensional barcodes, much more information can be printed on the slide glass 10 compared to when identification information and the like is entered by a technician.

The slide glass 10 is inserted into the cassette 3 in the slide glass insert unit 6. The cassette 3, which contains the inserted slide glass 10, is transported to the stain unit 7 by the cassette conveyor 5.

In the stain unit 7 (refer to FIG. 2), the smeared slide glass 10 is lifted from the slide glass slot 3a of the cassette 3, and methanol is dispensed to the stain suction-dispensing hole 3b of the cassette 3 by the first suction-discharge unit 7c. After the smeared slide glass 10 has been returned to the cassette 3, the cassettes housing the smeared slides 10 are moved one by one to the conveyor belt 7b by the feed member 7a. Then, the cassette 3 is transported to the second suction-discharge unit 7d by the conveyor belt 7b.

In the second suction-discharge unit 7d, the smeared slide glass 10 is lifted from the slide glass slot 3a of the cassette 3, and an air flow from the fan 7j directly on the smear surface of the slide glass 10 evaporates and dries the liquid on the smear surface for approximately 1~60 seconds. The time (immersion time) from when the smeared slide glass 10 is immersed in methanol by the first suction-discharge unit 7c until the slide glass 10 is lifted by the second suction-discharge unit 7d is approximately 20~120 seconds.

The staining process (May-Grünwald Giemsa double-stain process) is performed next. In the second suction-discharge unit 7d, after methanol has been suctioned and discharged from the stain suction-dispensing unit 3b of the cassette 3, the slide glass 10 is returned to the slide glass slot 3a of the cassette 3. May-Grünwald solution (main component: methanol 99%) is dispensed from the stain suction-dispensing hole 3b of the cassette 3, and the smeared slide glass 10 is immersed in the May-Grünwald solution. The May-Grünwald Giemsa double-stain process begins in this way. As the cassette 3 is transported by the conveyor belt 7b, the smeared slide glass 10 is immersed in the May-Grünwald solution in a staining process that lasts approximately 1~5 minutes. After the May-Grünwald solution is suctioned and discharged from the stain suction-dispensing hole 3b of the cassette 3, May-Grünwald dilution solution is dispensed to the stain suction-dispensing hole 3b of the cassette 3. As the cassette 3 is transported by the conveyor belt 7b, the smeared slide glass 10 is immersed in the May-Grünwald dilution solution for approximately 1~5 minutes. After the May-Grünwald dilution solution is suctioned and discharged from the stain suction-dispensing hole 3b of the cassette 3, Giemsa dilution solution is dispensed to the stain suction-dispensing hole 3b of the cassette 3. As the cassette 3 is transported by the conveyor belt 7b, the smeared slide glass 10 is immersed in the Giemsa dilution solution for approximately 1~20 minutes.

After the Giemsa dilution solution has been suctioned and discharged from the stain suction-dispensing hole 3b of the cassette 3, a washing fluid is dispensed and suctioned to/from the stain suction-dispensing hole 3b of the cassette 3 to wash the stained slide glass 10. Thereafter, the stained slide glass 10 is dried by the fan 7h.

The cassette 3, which contains the stained slide glass 10 that has been dried by the fan 7h, is sequentially transported from the conveyor belt 7b to the conveyor belt 8b side of the storage unit 8 by the delivery mechanism 7i shown in FIG. 2. Then, the cassette 3 is transported to the conveyor belt 8b of the storage unit 8 by the feed member 8a of the storage unit 8. In this way a cassette 3 brought from the feed member 8a is transported to the storage unit 8 and stored by the conveyor belt 8b.

After the cassette 3 has been transported to the transport end position of the stain unit 7 shown in FIG. 2, the cassette transport member 5a returns to the transport start position. In this way the cassette transport member 5a is capable of transporting a subsequent cassette 3. Then, the cassette transport member 5a transports the next cassette 3 to the slide glass insert unit 8 by pushing the side surface 3h of the next cassette 3.

Figure 7:
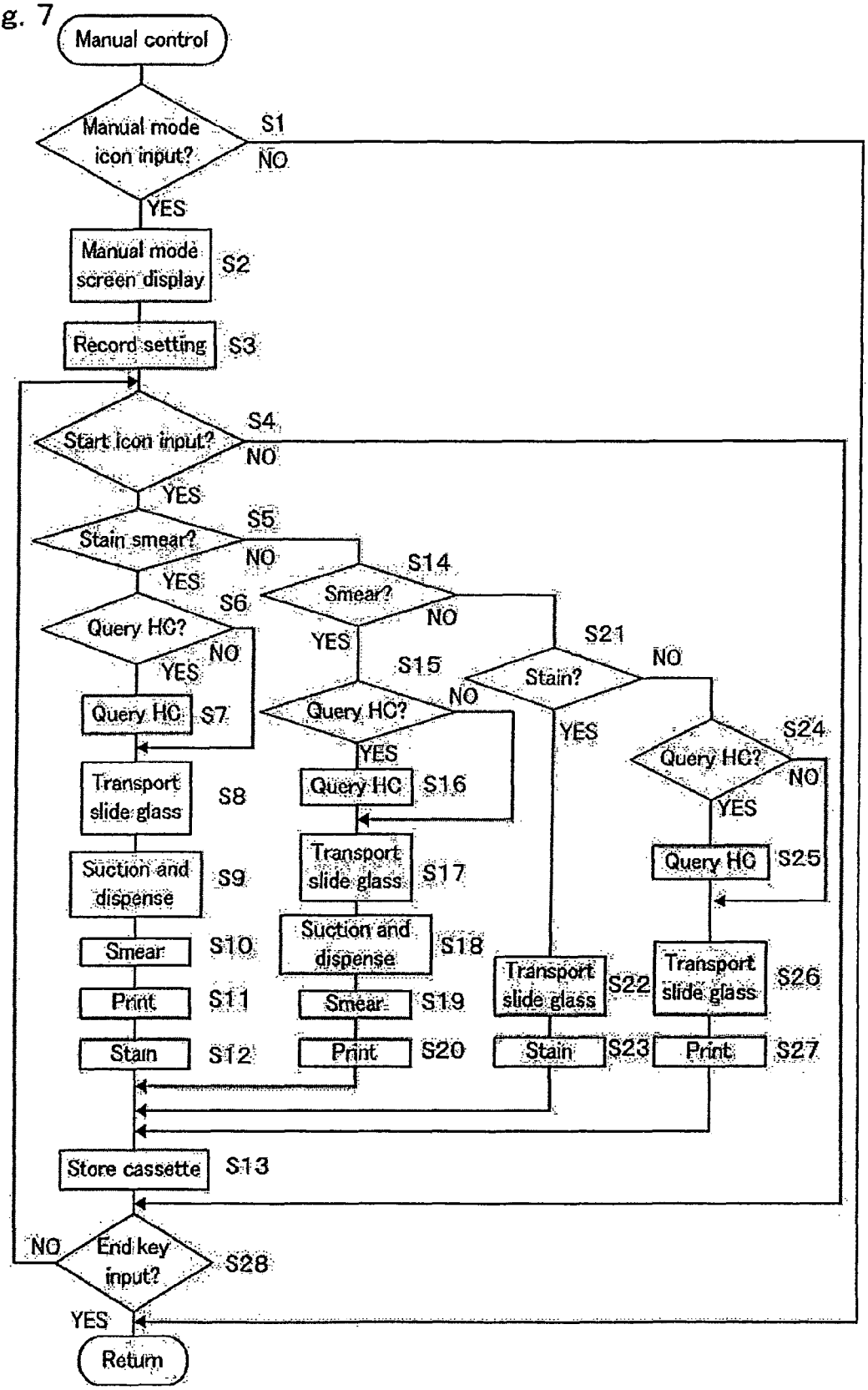
FIG. 7 is a flow chart illustrating the process by the controller of the sample preparing apparatus of the embodiment of the present invention.

The operation of the sample preparing apparatus 100 in the manual mode is described below. The manual mode is started by selecting the manual icon (not shown in the drawings) on the top screen displayed on the operation display unit 101. FIG. 7 is a flow chart illustrating the process performed by the controller 120 of the sample preparing apparatus 100 in manual mode. As shown in FIG. 7, the controller 120 determines whether or not there is manual icon input in step S1. When there is manual icon input, the manual mode starts.

Figure 8:
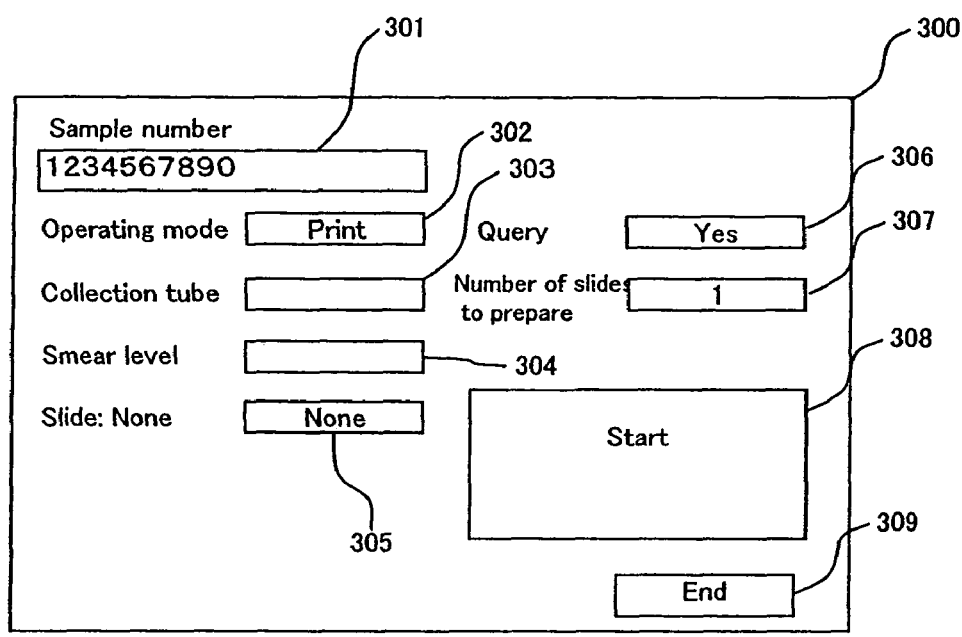
FIG. 8 shows the manual screen displayed on the operation display unit of the sample preparing apparatus of the embodiment of the present invention.

In step S2, the controller 120 executes a process to display the manual mode screen on the operation display unit 101. FIG. 8 shows the manual mode screen displayed on the operation display unit of the sample preparing apparatus of the embodiment of the present invention. As shown in FIG. 8, the manual mode screen 300 includes a sample number input part 301, mode selection part 302, collection tube selection part 303, smear level selection part 304, slide selection part 305, query selection part 306, number of slides to prepare selection part 307, start icon 308, and end key 309.

The sample number input part 301 is a region for inputting the sample number printed on the slide glass.

The mode selection part 302 is a region for selecting the mode. In the mode selection part 302, any mode can be selected from among a smear stain mode wherein smearing, printing and staining are performed, smear mode wherein smearing and printing are performed, but staining is not performed, stain mode wherein staining is performed, but smearing and printing are not performed, and print mode wherein printing is performed, but smearing and staining are not performed. When a user touches this region, the mode is switched. In the manual mode screen 300 shown in FIG. 8, the print mode is selected.

The collection tube selection part 303 is a region for selecting the type of sample container 151 used in the smear stain mode and smear mode. In the collection tube selection part 303, a closed container provided with a rubber stopper 151a, and a small sample tube capable of containing a minute amount of blood and not provided with a stopper 151a may be selected. In the manual mode screen 300 shown in FIG. 8, since the selected mode is the print mode and a sample container is not used, the region is blank.

The smear level selection part 304 is a region for selecting the smear level (condition) such as the speed of the drawing glass when the blood is smeared on the slide glass, the angle of the drawing glass relative to the slide glass and the like. In the smear level selection part 304, any of the levels 1~16 are selectable. In the manual mode screen 300 shown in FIG. 8, since the selected mode is the print mode and a smear is not performed, the region is blank.

The slide selection part 305 is a region for selecting the slide glass to be used from among slide glasses accommodated in two slide glass holders 2b (refer to FIG. 2). In the slide selection part 305, it is possible to select any selection among no slide, position 1 (slide glass holder 2b on the right side), and position 2 (the slide glass holder 2b on the left side). In the manual mode screen 300 shown in FIG. 8, the [No Slide] is selected.

The query selection part 306 is a region for selecting whether or not to send an inquiry to the host computer 107. In the query selection part 306, either [Query] or [No Query] can be selected. In the manual mode screen 300 shown in FIG. 8, the [Query] is selected.

The number of slides selection part 307 is a region for selecting the number of samples to be prepared. In the number of slides selection part 307, either one slide or two slides can be selected. In the manual mode screen 300 shown in FIG. 8, the [1 Slide] is selected.

The start icon 308 is an icon for starting an operation, such as the smear or stain operation.

The end key 309 is used to end the manual mode.

In step S3, the controller 120 executes a process (setting record) for a user to input to each region on the manual mode screen 300, and receive the selections.

In step S4, the controller 120 executes a process to determine whether or not there is input from the start icon 308.

When there is input from the start icon 308, the controller 120 determines whether or not the smear stain mode has been selected in mode selection part 302 in step S5. If the smear stain mode has been selected, the sample preparing apparatus 100 operates in the smear stain mode.

If the smear stain mode has not been selected, the controller 120 determines whether or not [Query] has been selected in the query selection part 306 in step S6.

If [Query] has been selected, the controller 120 sends an inquiry to the host computer 107 in step S7. Specifically, the sample number input in the sample number input part 301 is sent to the host computer 107, and identification information (sample collection date, reception number, name of patient providing the sample and the like) related to the sample number is received from the host computer 107. If [No Query] has been selected, the process of step S7 is not executed.

In step S8, the controller 120 executes a process for transporting the slide glass 10. By this process the slide glass 10 is transported from the slide glass holder 2b in the direction of the dispensing-smear position 90, horizontal position 91c for printing, slide glass insert unit 6, stain unit 7, and storage unit 8 similar to the operation in the sampler mode.

In step S9, the controller 120 executes a process for suctioning blood from the sample container 151, and dispensing the suctioned blood to the slide glass 10. By this process the suction dispensing mechanism 1 suctions the blood from the sample container 151, and dispenses the suctioned blood to the slide glass 10 disposed at the dispensing-smear position 90 similar to the operation in the sampler mode.

In step S10, the controller 120 executes a process for smearing the blood dispensed on the slide glass 10. By this process the smear unit 2 smears and dries the blood dripped onto the slide glass 10 similar to the operation in the sampler mode.

In step S11, the controller 120 executes a process for printing sample identification information on the slide glass 10. By this process the print unit 2g prints a two-dimensional barcode and text on the sample information print area of the slide glass 10 similar to the operation in the sampler mode when the query of step S7 has been performed. When the query has not been performed in step S7, only the sample number input in the sample number input part 301 is printed.

In step S12, the controller 120 executes a process for staining the smeared slide glass 10. By this process the stain unit 7 stains the blood smeared on the slide glass 10 similar to the operation in the sampler mode.

In step S13, the controller 120 executes a process for storing the cassette 3 in the storage unit 8. By this process the storage unit 8 stores the cassette 3 similar to the operation in the sampler mode.

When it is determined in step S5 that the smear stain mode has not been selected, then the controller 120 determines whether or not the smear mode has been selected in step S14. If the smear mode has been selected, the sample preparing apparatus 100 operates in the smear mode.

When the smear mode is selected, the controller 120 makes the same determination as in step S6 in step S15.

If [Query] has been selected, the controller 120 sends an inquiry to the host computer 107 in step S16 similar to that in step S7. If [No Query] has been selected, the process of step S16 is not executed.

In step S17, the controller 120 executes a process to transport the slide glass 10 similar to that of step S8.

In step S18, the controller 120 executes a process for suctioning blood from the sample container 151, and dispensing the suctioned blood to the slide glass 10 similar to step S9.

In step S19, the controller 120 executes a process for smearing the blood dispensed onto the slide glass 10 similar to step S10.

In step S20, the controller 120 executes a process for printing sample identification information on the slide glass 10 similar to step S11.

Then, the controller 120 executes the process of step S13.

When it is determined in step S14 that the smear mode has not been selected, then the controller 120 determines whether or not the stain mode has been selected in step S21. If the stain mode has been selected, the sample preparing apparatus 100 operates in the stain mode.

In step S22, the controller 120 executes a process for transporting the cassette 3m which accommodates a smeared slide glass, from the cassette holder 4 in the direction of the cassette conveyor 5, stain unit 7, and storage unit 8. The cassette containing the smeared slide glass is placed in the cassette holder 4 by the user.

In step S23, the controller 120 executes a process for staining the blood smeared on the slide glass 10 similar to step S12.

Then, the controller 120 executes the process of step S13.

When it is determined in step S21 that the stain mode has not been selected, then the controller 120 makes the same determination as in step S6 in step S24. When the stain mode has not been selected in step S21, it means the print mode has been selected, and the sample preparing apparatus 100 operates in the print mode.

If [Query] has been selected, the controller 120 sends an inquiry to the host computer 107 in step S25 similar to that in step S7. If [No Query] has been selected, the process of step S25 is not executed.

In step S26, the controller 120 executes a process to transport the slide glass 10 similar to that of step S8.

In step S27, the controller 120 executes a process for printing sample identification information on the slide glass 10 similar to step S11.

Then, the controller 120 executes the process of step S13.

In step S28, the controller 120 executes a process for determining whether or not there is input from the end key 309.

When there is input from the end key 309, the manual mode ends. If there is not input from the end key 309, the routine returns to step S4.

In the present embodiment, when a user selects the print mode and the sample preparing apparatus 100 is operated, the slide glass is completed without the sample smeared, but with the identification information printed. The user efficiently performs the examination work by manually preparing the smear sample on the slide glass and eliminating the conventional work of manual entry of identification information on the slide glass.

Although the stain unit 2 of the embodiment smears blood using a drawing glass 2c, the present invention is not limited to this method inasmuch as the present invention is also applicable to a sample preparing apparatus provided with a smear unit that smears blood using the spin method (centrifugal method).

Furthermore, although the sample preparing apparatus 100 of the above embodiment includes identification information, such as sample number, date, reception number, and patient name and the like in a two-dimensional barcode 10b, the present invention is not limited to this arrangement inasmuch as analysis results of the blood analyzer 6 may be included in the two-dimensional barcode, and only the sample number may be printed. A setting unit for setting the information to be printed may also be provided in the sample information print area 10a.

Although the sample preparing apparatus 100 of the present embodiment is a blood sample preparing apparatus that prepares blood smears, the present invention is not limited to this arrangement inasmuch as the present invention is also applicable to sample preparing apparatuses other than a blood sample preparing apparatus, such as a marrow sample preparing apparatus that prepares a sample of bone marrow fluid.

The sample preparing apparatus 100 of the present embodiment is capable of operating in any mode selected from among a smear stain mode wherein smearing and staining are performed, a smear mode wherein a smearing is performed but staining is not performed, stain mode wherein staining is performed but smearing is not performed, and print mode wherein only printing is performed, however, the present invention is not limited to this arrangement inasmuch as the present invention is also applicable to sample preparing apparatuses capable of operating in any mode selected from among a smear stain mode and print mode, and sample preparing apparatuses capable of operating in any mode selected from among a stain mode and print mode and the like.

The sample preparing apparatus of the present invention is also capable of operating in any mode selected from among a print mode and a mode that performs smearing but does not perform staining or printing. The apparatus of the present invention is also capable of operating in any mode selected from among a print mode and a mode that performs staining but does not perform smearing or printing. The apparatus of the present invention is also capable of operating in any mode selected from among a print mode and a mode that performs smearing and staining but does not perform printing.

Furthermore, although the sample preparing apparatus 100 of the present embodiment is provided with a stain unit 7, the present invention is not limited to this arrangement inasmuch as the present invention is also applicable to a sample preparing apparatus that is not provided with a stain unit 7. In this case, the sample preparing apparatus is capable of operating in any mode selected from among a smear mode and print mode.

Furthermore, although the sample preparing apparatus 100 of the present embodiment is provided with a smear unit 2, the present invention is not limited to this arrangement inasmuch as the present invention is also applicable to a sample preparing apparatus that is not provided with a smear unit 2. In this case, the sample preparing apparatus is capable of operating in any mode selected from among a stain mode and print mode. The present invention is also applicable to sample preparing apparatuses that suitably combine the previously described modes.

The embodiment disclosed above has been described by way of examples in all aspects and is not to be considered as restrictive in any sense. The present invention may be variously modified insofar as such modification is within the scope and equivalences of the claims.

What is claimed is:

1. A sample preparing apparatus comprising:
   a smear forming unit configured for performing smearing in which a sample is smeared on a slide glass;
   a printer configured for performing printing in which sample identification information is printed on the slide glass; and
   a controller configured for operating the sample preparing apparatus under a plurality of operating modes that comprises a print mode and a smear mode,
   the wherein controller is configured to selectively activate the printer and the smear forming unit so as to implement the printing but not the smearing under the print mode and to implement both printing and smearing under the smearing mode, the modes being selected by a mode selector.

2. The sample preparing apparatus of claim 1 further comprising:
   a stain unit configured for performing staining in which a smear formed on the slide glass is stained,
   wherein the plurality of operating modes further comprises a smear staining mode, and the controller selectively activates the smear forming unit, the printer, and the stain unit so as to implement all of the smearing, staining and printing under the smear staining mode.

3. The sample preparing apparatus of claim 2,
   wherein the plurality of operating modes further comprises a stain mode, and the controller implements the staining but not the smearing or printing under the stain mode.

4. The sample preparing apparatus of claim 1, further comprising;
   a sample information input unit configured for receiving the inputted identification information; and
   a communicator configured for performing communication with an external device, wherein the communicator comprises:
      a transmission unit configured for sending the inputted identification information to the external device for storage thereof; and
      a reception unit configured for receiving from the external device the identification information modified for printing;
   wherein the printer prints the modified identification information on the slide glass.

5. The sample preparing apparatus of claim 4, wherein the identification information comprises a sample number, wherein the modified identification information comprises the sample number and a patient name, and wherein the printer prints a barcode representing the modified identification information.

6. The sample preparing apparatus of claim 4, wherein the barcode comprises a two-dimensional barcode.

7. The sample preparing apparatus of claim 4, wherein the printer comprises a thermal transfer printer.

8. A sample preparing apparatus comprising:
- a sample identification information input unit configured for receiving inputted sample identification information;
- a communicator configured for performing communication with an external device, wherein the communicator comprises:
  - a transmission unit configured for sending the inputted sample identification information to the external device for storage thereof; and
  - a reception unit configured for receiving from the external device the sample identification information and additional sample information;
- a smear forming unit configured for performing smearing in which a sample is smeared on a slide glass;
- a printer configured for performing printing in which a two-dimensional barcode representing the sample identification information and the additional information is printed on the slide glass; and
- a printer configured for performing printing in which a two-dimensional barcode representing the sample identification information and the additional information is printed on the slide glass; and
- a controller configured for operating the sample preparing apparatus under a plurality of operating modes that comprises a print mode and a smear mode, the wherein controller is configured to selectively activate the printer and the smear forming unit so as to implement the printing but not the smearing under the print mode and to implement both printing and smearing under the smear mode, the modes being selected by a mode selector.

9. The sample preparing apparatus of claim 8, wherein the two-dimensional barcode comprises a sample number as the sample identification information, and a patient name as the additional information.

10. The sample preparing apparatus of claim 8, wherein the printer comprises a thermal transfer printer.

11. The sample preparing apparatus of claim 8 further comprising:
- a stain unit configured for performing staining in which a smear formed on the slide glass is stained,
- wherein the plurality of operating modes further comprises a smear staining mode, and the controller selectively activates the smear forming unit, the printer, and the stain unit to implement all of the smearing, printing and staining under the smear staining mode.

12. The sample preparing apparatus of claim 11, wherein the plurality of operating modes further comprises a stain mode, and the controller implements the staining but not the printing or smearing under the stain mode.

* * * * *